United States Patent [19]

Stafford et al.

[11] Patent Number: 5,395,400
[45] Date of Patent: Mar. 7, 1995

[54] HEATED HEADGEAR

[75] Inventors: Thomas Stafford; Christl Treptow, both of Mission Viejo, Calif.

[73] Assignee: Christl D. Treptow, Mission Viejo, Calif.

[21] Appl. No.: 97,727

[22] Filed: Jul. 26, 1993

Related U.S. Application Data

[63] Continuation of Ser. No. 839,386, Feb. 21, 1992, abandoned.

[51] Int. Cl.6 .............................................. A61F 7/00
[52] U.S. Cl. .................................. 607/109; 607/114; 2/209
[58] Field of Search ............... 128/399, 400, 402, 403, 128/379, 380, 384; 62/570, 259.3; 126/263, 204; 2/209, 7, 171.2, 171.5, 171.8, DIG. 11; 607/108, 109, 110; 4/112, 14, 40

[56] References Cited

U.S. PATENT DOCUMENTS

| | | |
|---|---|---|
| 527,922 | 10/1894 | Backstrom et al. . |
| 1,169,123 | 1/1916 | Burns .................................. 128/402 |
| 1,567,931 | 12/1925 | Epler .................................. 128/402 |
| 2,405,326 | 8/1946 | Plotsky .................................. 2/209 |
| 3,491,761 | 1/1970 | Baker .................................. 128/402 |
| 3,696,814 | 10/1972 | Umemoto .................................. 128/402 |
| 3,796,855 | 3/1974 | Brown et al. .................................. 128/399 |
| 3,900,035 | 8/1975 | Welch et al. .................................. 128/403 |
| 4,055,188 | 10/1977 | Pelton .................................. 128/402 |
| 4,190,054 | 2/1980 | Brennan .................................. 128/402 |
| 4,204,543 | 5/1980 | Henderson .................................. 128/402 |
| 4,425,917 | 1/1984 | Kuznetz .................................. 128/403 |
| 4,688,572 | 8/1987 | Hubbard et al. .................................. 128/402 |
| 4,776,042 | 10/1988 | Hanson et al. .................................. 128/380 |
| 4,856,651 | 8/1989 | Francis .................................. 128/403 |

*Primary Examiner*—Mark S. Graham
*Attorney, Agent, or Firm*—Sherman & Sherman

[57] ABSTRACT

A headgear garment has pockets for receiving exothermic heat packets to provide an active heat-generating source proximate to the ears of a wearer. The garment includes a garment body having pockets for receiving exothermic heat-generating packets and a means for securing the garment to the wearer's head. The securing means may be the structural configuration of the garment itself. The pockets are constructed of a breathable material to allow the exothermic heat-generating packets to provide heat and are placed proximate to the wearer's ears when worn. An insulation material is placed between the pockets and the ears to protect the ears from any excess heat generated by the exothermic packets. The shown embodiments include earmuffs, headbands, including a helmet headband and a straight headband, and a hat.

13 Claims, 3 Drawing Sheets

HEATED HEADGEAR

This is a file wrapper continuation of application Ser. No. 839,386, filed Feb. 21, 1992, abandoned, for HEATED HEADGEAR.

FIELD OF THE INVENTION

The present invention relates to headwear garments such as hats, earmuffs, and headbands and, more particularly, to a system for introducing pockets into those garments to allow exothermic heat-generating packets to be used in conjunction with that headgear.

BACKGROUND OF THE INVENTION

Typical exothermic heat-generating pads are disclosed in a variety of patents issued within the last 15 years or so.

Generally, such products contain an exothermic composition such as a composition of iron powder, active carbon, salt, sawdust, water, and other components. Those components are normally blended to provide an exothermic chemical reaction when exposed to air. The components generate heat which may be exploited to warm various parts of the body.

The exothermic composition may be contained within a porous, breathable bag composed of a woven fabric. The porous bag is normally stored within a nonventilating plastic outer bag. When the outer bag is opened, the contents of the porous bag are exposed to air, thereby activating the exothermic properties of the components contained within.

Typical patents relating to such exothermic heat-generating packets or pads include, by way of example, U.S. Pat. Nos. 3,976,049; 4,268,272; and 4,282,005. Each patent relates generally to the same type of end product, but discloses a different combination of exothermic heat-generating ingredients. Such products will produce heat for a period of between 12 and 24 hours at temperatures up to 160° F., and can be provided in a variety of different sizes deemed to be convenient for application to the body. Such products have been advantageously used by a variety of sports enthusiasts who are exposed to frigid air, as well as by the general public, for example, in keeping warm during outdoor sporting events such as football games and the like.

Such products may be contained in the pockets of outer garments or in shoes or boots and so forth. Unfortunately, outer garments, shoes, boots, and the like do not always provide the most efficient means for receiving such exothermic heating pads, and clearly, they do not provide convenient means for wearing such pads adjacent certain joints or extremities for warming or therapeutic purposes.

Alternatively, hats, headbands, and earmuffs are known which provide only protection and thermal insulation to the wearer's head. It is commonly known that a large percentage of a human being's body heat escapes through the head area. To protect against hypothermia in cold activities, headgear is commonly recommended. However, this headgear generally provides only a passive heat insulation which merely limits the amount of heat allowed to escape.

Additionally, devices are known which provide temperature therapy to different areas of the head. Examples are U.S. Pat. Nos. 3,491,761; 3,796,855; 4,190,054; and 4,204,543. However, none of these devices provide a system for applying an active warming element in combination with nonobtrusive headgear which may be used by enthusiasts engaged in sports environments where hypothermia might be experienced.

OBJECTS OF THE INVENTION

It is therefore an object of the present invention to provide a system of combining exothermic heat packets with protective headgear;

It is a further object of the present invention to provide headgear adaptable for receiving exothermic packets in a portable manner and for providing heat protection in strenuous activities in extreme environments; and It is yet a still further object of the present invention to provide an improved system for protecting athletes from hypothermia.

SUMMARY OF THE INVENTION

These and other objects of the present invention are provided by a headgear garment having pockets for receiving exothermic heat packets to provide an active heat-generating source proximate to the ears of a wearer.

In each of the shown embodiments the garment includes a garment body having pockets for receiving exothermic heat-generating packets and a means for securing the garment to the wearer's head. The securing means may be the structural configuration of the garment itself.

The pockets used in each of the shown embodiments are constructed of a breathable material which has sufficient breathability to allow the exothermic heat-generating packets to provide a temperature between approximately 130° and 160° F. The pockets are stitched into the garment so that the pockets are placed proximate the wearer's ears when worn and the exothermic packets are allowed to provide heat to the ears.

In each of the shown embodiments, an insulation material is positioned between the pockets and the ears. The insulation provides thermal protection to the wearer's ears when the garment is worn in order to protect the ears from any excess heat generated by the exothermic packets. The shown embodiments include earmuffs, headbands, including a helmet headband and a straight headband, and a hat.

BRIEF DESCRIPTION OF THE DRAWINGS

The present invention, both as to its organization and manner of operation, together with further objects and advantages, may be understood by reference to the following drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein.

Figure 1:
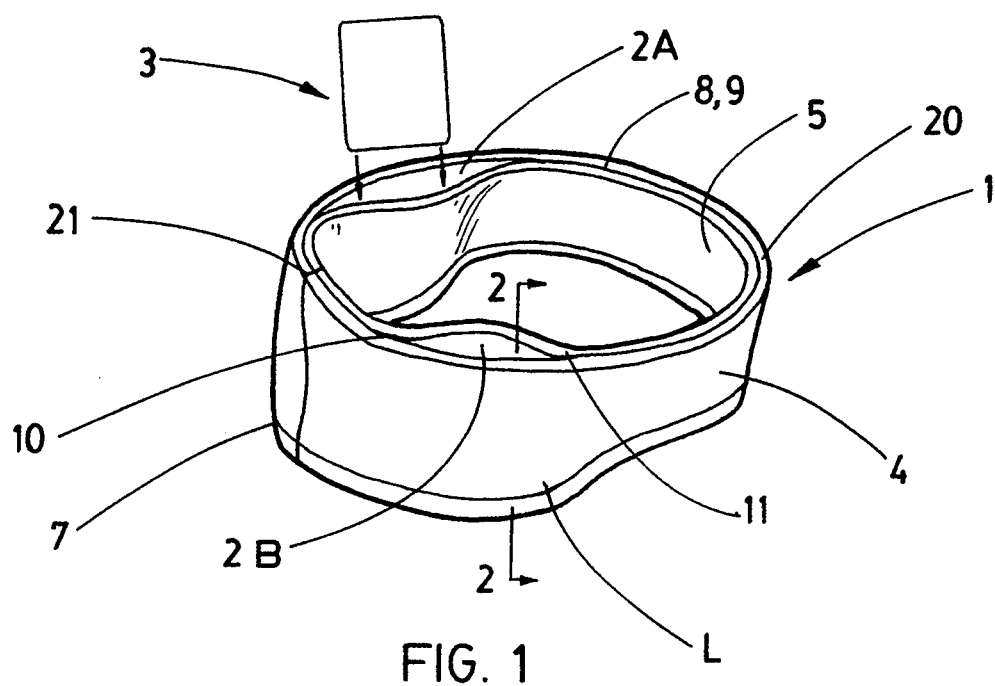
FIG. 1 is an illustration of a helmet headband embodiment of the present invention.

A first preferred embodiment of the invention is illustrated in FIG. 1. Therein, the headgear garment 1 is a helmet headband.

Conventional headbands have been used for their insulative capacities by merely providing a barrier between the head of the wearer and the extreme cold environments in which the wearers may find themselves. For instance, conventional helmet headbands provide insulative protection against cold winds and snows for skiers, etc.

The helmet headband of FIG. 1, however, in addition to the insulative aspects of the headgear garment, provides an active heat-generating source proximate to the ears of the wearer. As can be seen in FIG. 1, the helmet headband 1 includes pockets 2a, 2b for allowing the introduction of an exothermic heat-generating packets 3.

As discussed above, when the packet 3 is exposed to air, an exothermic chemical reaction starts and the packet begins to generate heat. As long as the packet is continuously exposed to the air, the exothermic reaction will continue, and heat will continue to be radiated until it expires. Additionally, the rate of the exothermic reaction can be controlled by the amount of air which the packet is allowed to access and, therefore, the amount of heat which the packet is made to generate.

The outer layers 4, 5 of the helmet headband embodiment shown in FIG. 1 may be constructed from any flexible fabric which is breathable. In the preferred embodiment of the invention, the outer layers 4, 5 are currently being constructed of "turtle fleece TM," but may also be constructed alternatively of any type of fleece or knit, or other breathable material.

The pockets 2a, 2b are stitched inside the outer layers 4, 5. The pockets 2a, 2b are also constructed of a breathable material and, in the preferred embodiment, they are constructed of a cotton fabric which is loosely woven.

Figure 2:
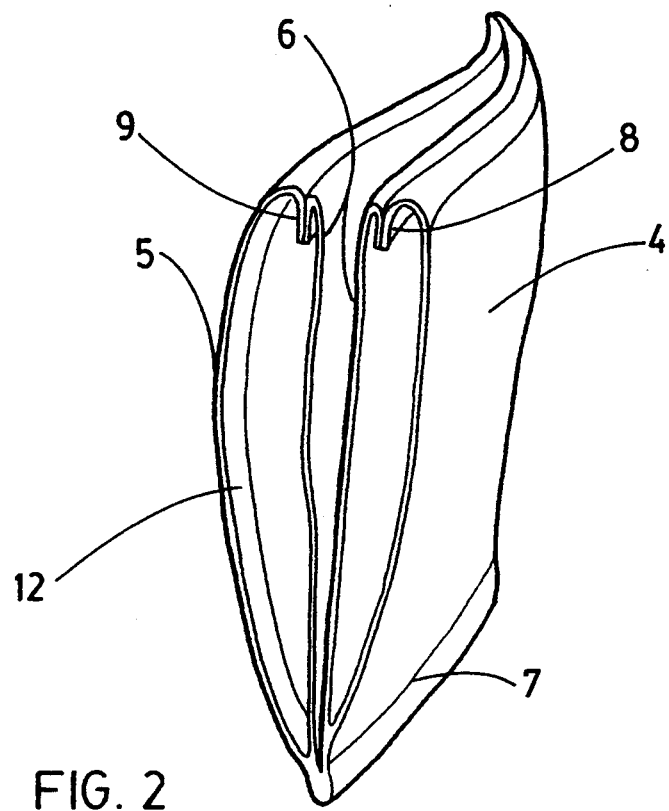
FIG. 2 is a cross-sectional view of the headband embodiment of FIG. 1 cut along the lines 2—2.

FIG. 2 is a cross-sectional cutaway illustration of the helmet headband shown in FIG. 1. As shown in FIG. 2, the inside outer layer 5 and the outside outer layer 4 of the helmet headband are constructed of a turtle fleece material. The pocket fabric 6 is a loosely woven cotton.

The fabric layers are stitched together at seams 7, 8, and 9. Seams 8 and 9 join as a single seam at the borders of the pockets shown as 10 and 11 in FIG. 1.

In addition to the layers discussed above, a further layer 12 may be included in the headband embodiment. The layer 12 flows between the pocket layers 6 and the inside outer layer 5 which comes into contact with the wearer. This layer 12 is an insulating layer which provides both additional thermal insulation to the head and thermal protection between the wearer's ears and the exothermic heat-generating packet carried within the headband. In the preferred embodiment, the inner layer 12 is constructed from Thinsulate TM light loft insulation, which is commonly available from 3M Corporation. The Thinsulate TM material is stitched into the garment at seams 9 and 7.

In the preferred embodiment, the Thinsulate TM layer 12 is only provided in a single layer with the pocket layers 6 provided externally of the Thinsulate TM 12. However, further embodiments are envisioned within the scope of the invention wherein the Thinsulate TM layer is provided on both sides of the pockets or wherein the Thinsulate TM layer is merely provided on the external side of the pockets.

Figure 3:
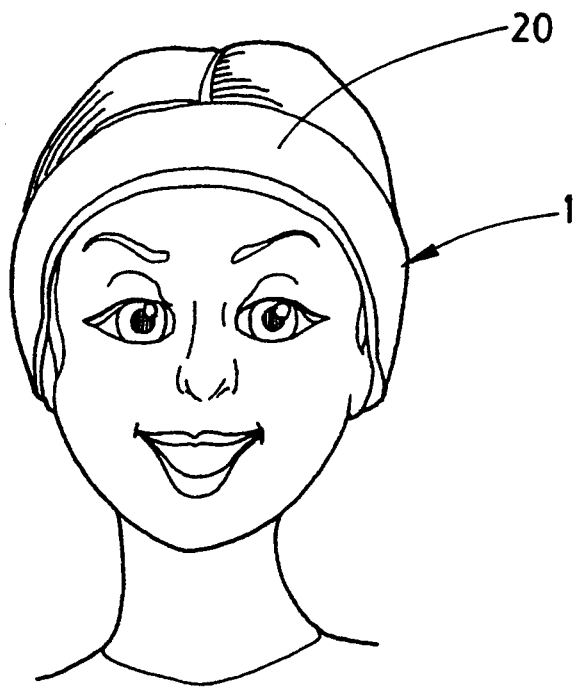
FIG. 3 is an illustration of the headband embodiment of FIG. 1 being worn by a wearer.

FIG. 3 illustrates the helmet headband being worn by a wearer. As shown in FIG. 3, the front of the headband 20 extends over the wearer's forehead, and the rear of the headband 21 (not shown) extends around the back of the wearer's skull. When used in this configuration, the pockets 2a and 2b are fitted over the wearer's ears with the exothermic heat generation packets 3 installed inside.

Because of the flexible resiliency of the fabric from which the headband is constructed, the headband provides a snug fit around the wearer's ears, forehead, and rear of the head when worn in the manner shown in FIG. 3. Additionally, since the seams 7, 8, and 9 provide less resiliency to the headband flexibility. As such, when the headband is worn, the seams 8 and 9 close over the pockets, providing a tight fit and effectively sealing the exothermic heat-generating packet 3 within the pocket enclosure.

Additionally, the snug fit of the headband maintains the headband in place on the wearer's head, even in higher winds as experienced by downhill skiers.

Figure 4:
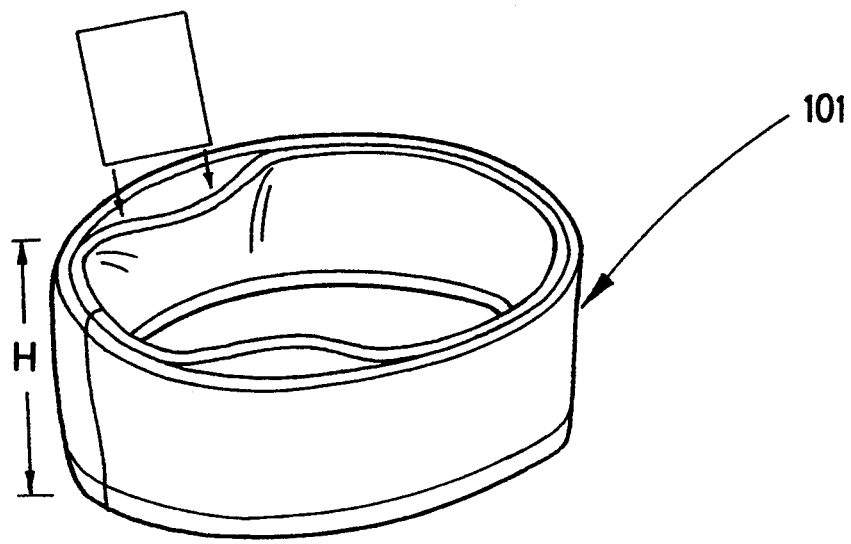
FIG. 4 is an illustration of a straight headband embodiment of the present invention.

A further headband embodiment of the invention is shown in FIG. 4. Therein, the headband 101 is a straight headband. The straight headband 101 shown in FIG. 4 and the helmet headband 1 shown in FIG. 1 are distinguishable by the continuous height h around the circumference of the headband 101.

As seen in FIG. 1, the helmet headband 1 has a varying height which lessens at the front of the headband. This difference in height changes at the lobes L in front of the pockets 2a, 2b. At the front 20, the height of the headband is somewhat less to provide less interference with the user's forehead and to ensure that the headband does not extend down over the user's eyes. However, the lobes L will sometimes provide drag when the user is facing into the wind, and the lobes L will lift from the user's ears.

Figure 5:
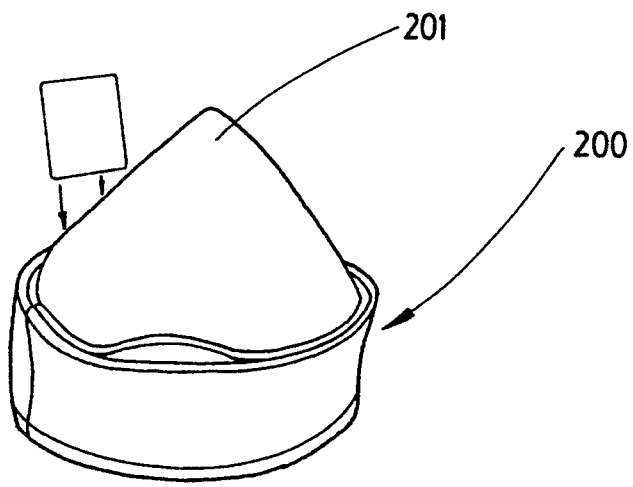
FIG. 5 is an illustration of a hat embodiment of the present invention.

A further preferred embodiment of the invention is shown in FIG. 5. In this embodiment, the headgear garment is a hat 200. The hat 200 shown in FIG. 5 is similar to the straight headband 101 illustrated in FIG. 4 and the helmet headband 1 illustrated in FIG. 1. In the hat 200, the inside outer layer 5 extends up and around the worker's head, creating a peak 201. This type of hat provides the added insulative effect of covering the user's head.

Figure 6:
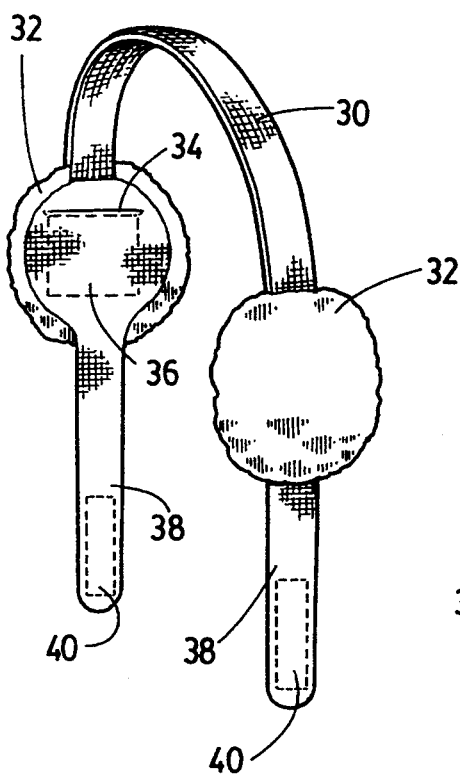
FIG. 6 is an illustration of earmuffs embodying the present invention.
Figure 7:
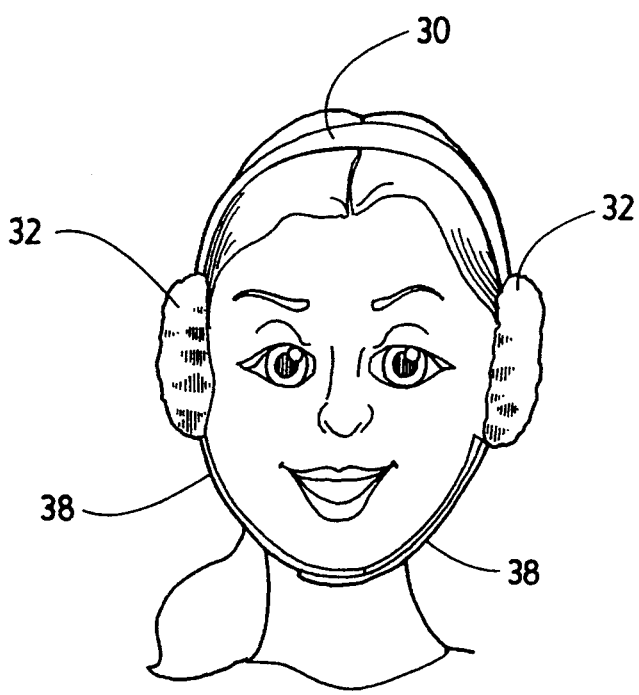
FIG. 7 is an illustration of the earmuff embodiment of the invention shown in FIG. 6 as worn by a wearer.

A fourth embodiment of the invention is shown in FIGS. 6 and 7. This fourth embodiment 30 is an earmuff configuration 30 which comprises a pair of ear covers 32. Each ear cover 32 is provided with an access slit 34 leading into a pocket 36 of substantially rectangular or square configuration and adapted to receive a correspondingly shaped exothermic heat-generating packet.

The earmuffs 32 may also be provided with a pair of chin straps 38, each of which provides a Velcro TM fastening means 40 or other similar fastening means to permit retention of the earmuffs in a conventional manner around the head for protection of the ears, as illustrated in FIG. 7.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A headgear garment having receiving pockets for receiving exothermic heat packets to provide an active heat-generating source proximate to ears of a wearer, the headgear garment including flexibly resilient fabric having upper and lower seams stitchedly connecting the receiving pockets within the garment, the upper seam splitting into two pocket border seams to form an opening where the receiving pockets are stitched to the upper seam, the seams having less resiliency than the flexibly resilient fabric such that the border seams are pulled taut and the opening is sealed when the garment body is worn on the wearer's head.

2. A headgear garment comprising:
   exothermic heat-generating packets;
   a garment body including flexibly resilient fabric stitched together to form upper and lower seams;
   receiving pockets attached to the garment body for accepting the exothermic heat-generating packets, the receiving pockets stitchedly connected to the upper and lower seams within the garment body, the upper seam splitting into two pocket border seams to form an opening where the receiving pockets are stitched to the upper seam, the seams having less resiliency than the flexibly resilient fabric such that the border seams are pulled taut and the opening is sealed when the garment body is worn on a user's head; and
   a means for securing the garment body to a user's head, the securing means placing the receiving pockets proximate a user's ears such that the exothermic heat-generating packets provide heat to the ears.

3. The garment of claim 2, further comprising an insulation material, the insulation material being positioned between the receiving pockets and the ears when the garment is worn to provide thermal protection for the wearer's ears from the exothermic heat-generating packets.

4. The garment of claim 2, wherein the exothermic heat-generating packets are replaceable.

5. The garment of claim 2, wherein the receiving pockets are constructed of a breathable material having sufficient breathability to allow the exothermic heat-generating packets to provide a temperature between approximately 130° and 160° F.

6. The garment of claim 5, wherein the breathable receiving pockets are constructed of woven cotton fabric.

7. The garment of claim 2, wherein the means for securing is a headband.

8. The garment of claim 7, wherein the headband is constructed of a flexible fabric providing an elastic positioning around the head and over the ears.

9. The garment of claim 7, wherein the headband is a helmet headband.

10. The garment of claim 7, wherein the headband is a straight headband.

11. The garment of claim 2, wherein the garment is a hat including a headband fitting around the wearer's ears and a peak fitting over the wearer's head.

12. A headgear garment comprising:
    a garment body including flexibly resilient fabric stitched together to form upper and lower seams;
    exothermic heat-generating packets;
    receiving pockets attached to the garment body for accepting the replaceable exothermic heat-generating packets, the receiving pockets stitchedly connected to the upper and lower seams within the garment body, the upper seam splitting into two pocket border seams to form an opening where the receiving pockets are stitched to the upper seam, the seams having less resiliency than the flexibly resilient fabric such that the border seams are pulled taut and the opening is sealed when the garment body is worn on the user's head, the receiving pockets being constructed of a breathable material having sufficient breathability to allow the exothermic heat-generating packets to provide a temperature between approximately 130° and 160° F.;
    a means for securing the garment body to a user's head, the securing means placing the receiving pockets proximate a user's ears such that the exothermic heat-generating packets provide heat to the ears; and
    an insulation material positioned between the receiving pockets and the ears when the garment is worn to provide thermal protection for the user's ears from any excess heat generated by the exothermic heat-generating packets.

13. A headgear garment, comprising:
    a garment body having an inside outer layer and an outside outer layer, the inside outer layer and the outside outer layer being constructed from a breathable flexibly resilient fabric, the inside outer layer and the outside outer layer being stitched together to form upper and lower seams;
    at least two exothermic heat-generating packets;
    two receiving pockets stitchedly attached within the garment body between the inside outer layer and the outside outer layer, the exothermic heat-generating packets being replaceably received within the receiving pockets, the receiving pockets being stitchedly attached to the upper and lower seams, the receiving pockets fitting proximate a user's ears such that the exothermic heat-generating packets installed within the receiving pockets provide heat to the user's ears when the garment body is worn over a user's head, the upper seam splitting into two pocket border seams to form an opening where the receiving pockets are stitched to the upper seam, the seams having less resiliency than the flexibly resilient fabric such that the border seams are pulled taut and the opening is sealed when the garment body is worn on the user's head, the receiving pockets being constructed of a breathable material having sufficient breathability to allow the exothermic heat-generating packets to provide a temperature between approximately 130° and 160° F.; and
    an insulation material positioned between the receiving pockets and the inside outer layer such that the insulation material provides thermal protection for the user's ears from any excess heat generated by the exothermic heat-generating packets.

* * * * *